(12) United States Patent
Saito et al.

(10) Patent No.: US 6,399,340 B1
(45) Date of Patent: Jun. 4, 2002

(54) VECTOR DERIVATIVES OF GLUCONOBACTER PLASMID PF4

(75) Inventors: Yoshimasa Saito, Kawanishi; Yuji Noguchi, Aichi; Koji Yoshikawa, Ushiku; Shinsuke Soeda, Nagoya, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/509,565

(22) PCT Filed: Oct. 13, 1998

(86) PCT No.: PCT/JP98/04611
§ 371 (c)(1),
(2), (4) Date: Jun. 23, 2000

(87) PCT Pub. No.: WO99/20772
PCT Pub. Date: Apr. 29, 1999

(30) Foreign Application Priority Data

Oct. 16, 1997 (JP) .............................................. 9-303395

(51) Int. Cl.[7] .............................. C12P 7/60; C12P 21/06; C12N 15/00; C12N 9/04; C12N 1/20; C07H 21/02; C07H 21/04

(52) U.S. Cl. .................... 435/138; 435/320.1; 435/190; 435/69.1; 435/252.3; 536/23.1; 536/23.2

(58) Field of Search .......................... 435/320.1, 252.3, 435/69.1, 190, 138; 536/23.1, 23.2

(56) References Cited

U.S. PATENT DOCUMENTS

| | | | |
|---|---|---|---|
| 5,753,481 A | 5/1998 | Niwa et al. | 435/190 |
| 5,834,263 A | 11/1998 | Niwa et al. | 435/138 |
| 5,861,292 A | 1/1999 | Niwa et al. | 435/190 |
| 5,888,786 A | 3/1999 | Niwa et al. | 435/138 |

FOREIGN PATENT DOCUMENTS

WO WO95/23220 * 8/1995

OTHER PUBLICATIONS

Brantl et al. Mol Microbiol (1992) 6(23):3501–3510.*
Cheah et al. Plasmid (1987) 18(2):127–134.*
Hanahan J Mol Biol (1983) 166(4):557–580.*

* cited by examiner

Primary Examiner—Rebecca E. Prouty
Assistant Examiner—David J Steadman
(74) Attorney, Agent, or Firm—Oblon, Spivak, McClelland, Maier & Neustadt, P.C.

(57) ABSTRACT

A DNA derived from plasmid pF4, which contains a region involved in the control of autonomous replication in a bacterial cell belonging to the genus Gluconobactor, with or without a part of the polynucleotide region not essential for the autonomous replication therein, particularly, the same DNA comprising, as the region involved in the control of autonomous replication in the bacterial cell belonging to the genus Gluconobactor, a part or the entirety of the polynucleotide of nucleotide No. 2897–3969 region of Sequence Listing SEQ:ID No. 1. A plasmid vector containing this DNA, transformant transformed with this plasmid vector, and a method for producing a physiologically active substance comprising culturing this transformant. The full length nucleotide sequence of plasmid pF4 and the region containing DNA involved in the control of automonous replication in the bacterial cell belonging to the genus Gluconobactor were specified, whereby the region not essential for the automonous replication could be removed to provide a shortened pF4. The shortening of the region in the vector for autonomous replication increases the remaining region of the vector and allows incorporation of many structural genes into the vector. Consequently, the vector can have many functions.

20 Claims, 7 Drawing Sheets

VECTOR DERIVATIVES OF GLUCONOBACTER PLASMID PF4

TECHNICAL FIELD

The present invention relates to a DNA involved in the function of controlling autonomous replication in a bacterial cell belonging to the genus Gluconobactor, a plasmid vector containing said DNA, a transformant transformed with said plasmid vector and a method for producing a physiologically active substance such as an enzyme, comprising culturing said transformant.

BACKGROUND ART

The plasmids belonging to the genus Gluconobactor are known to include pF2, pF3, pF4, shuttle vector pFG5B (combined plasmid of pHSG298 (plasmid of *Escherichia coli*) and pF2), pFG14A (combined plasmid of pHSG298 and pF3), pFG15A (combined plasmid of pHSG298 and pF4) (all of which disclosed in WO95/23220) and the like. With regard to these plasmids, however, the specific position of the plasmid that controls autonomous replication in the bacterial cell belonging to the genus Gluconobactor or the sequence thereof has not been known at all.

DISCLOSURE OF THE INVENTION

An object of the present invention is to specify the region of the nucleotide sequence of plasmid pF4 derived from the genus Gluconobactor (*Gluconobactor oxydans* T-100; see W095/23220), which is necessary for replication in the bacterium belonging to the genus Gluconobactor. Another object of the present invention is to provide a plasmid vector containing a region essential for the replication but is free of the region not essential for the replication, or compact pF4, and a transformant transformed with this plasmid vector. A further object of the present invention is to provide a plasmid vector containing, besides the above-mentioned region, a structural gene capable of expression in a host cell (hereinafter this plasmid is also referred to as recombinant expression vector), a transformant transformed with this recombinant expression vector and a method for producing a physiologically active substance, which comprises culturing this transformant and harvesting a physiologically active substance, such as enzyme and the like, which has been expressed in the culture.

The present inventors have conducted intensive studies in an attempt to solve the above-mentioned problems, and succeeded in specifying the region of the nucleotide sequence of plasmid pF4 derived from the genus Gluconobactor, which is essential for the replication in bacterial cells belonging to the genus Gluconobactor. They have also succeeded in shortening plasmid pF4 by leaving the region essential for the replication but removing a part or the whole of the region not essential for the replication, as well as in preparing a vector containing the shortened plasmid and a recombinant expression vector additionally containing a structural gene, which resulted in the completion of the present invention.

Accordingly, the present invention provides the following.

(1) A DNA derived from plasmid pF4, which contains a region involved in the control of autonomous replication in a bacterial cell belonging to the genus Gluconobactor, with or without a part of the polynucleotide region not essential for the autonomous replication therein, except pF4 itself.

(2) The DNA of the above (1), substantially comprising, as the region involved in the control of autonomous replication in the bacterial cell belonging to the genus Gluconobactor, a part or the entirety of the polynucleotide of nucleotide Nos. 2897–3969 region of Sequence Listing SEQ:ID No. 1, or substantially comprising a part or the entirety of polynucleotide of the nucleotide Nos. 2897–3969 region of Sequence Listing SEQ:ID No. 1, wherein at least one nucleotide has been deleted, substituted, added or inserted.

(3) A DNA substantially having a nucleotide sequence depicted in Sequence Listing SEQ:ID No. 1 or a DNA having the same nucleotide sequence depicted in Sequence Listing SEQ:ID No. 1 except that at least one nucleotide has been deleted, substituted, added or inserted.

(4) A plasmid vector comprising the DNA of the above (1) or (2).

(5) The plasmid vector of the above (4), comprising a DNA involved in autonomous replication in a bacterial cell belonging to the genus Gluconobactor and a DNA involved in autonomous replication in a host other than the bacterial cell belonging to the genus Gluconobactor, particularly *Escherichia coli*.

(6) The plasmid vector of the above (4) or (5), comprising, within the plasmid vector, a structural gene capable of expression in a host.

(7) The plasmid vector of the above (6), wherein the structural gene capable of expression in the host encodes a physiologically active substance.

(8) The plasmid vector of the above (7), wherein the physiologically active substance is L-sorbose dehydrogenase and/or L-sorbosone dehydrogenase.

(9) A transformant transformed with the plasmid vector of any of the above (4)–(8).

(10) A method for producing a physiologically active substance, comprising culturing the transformant transformed with the plasmid vector of the above (7) to express the physiologically active substance, and harvesting the physiologically active substance.

(11) A method for producing L-sorbose dehydrogenase and/or L-sorbosone dehydrogenase, comprising culturing a transformant transformed with the plasmid vector of the above (8) to express L-sorbose dehydrogenase and/or L-sorbosone dehydrogenase, and harvesting the L-sorbose dehydrogenase and/or L-sorbosone dehydrogenase.

(12) A method for producing 2-keto-L-gulonic acid, comprising culturing a transformant transformed with the plasmid vector of the above (8) to express L-sorbose dehydrogenase and L-sorbosone dehydrogenase.

BEST MODE FOR EMBODYING THE INVENTION

Figure 1:
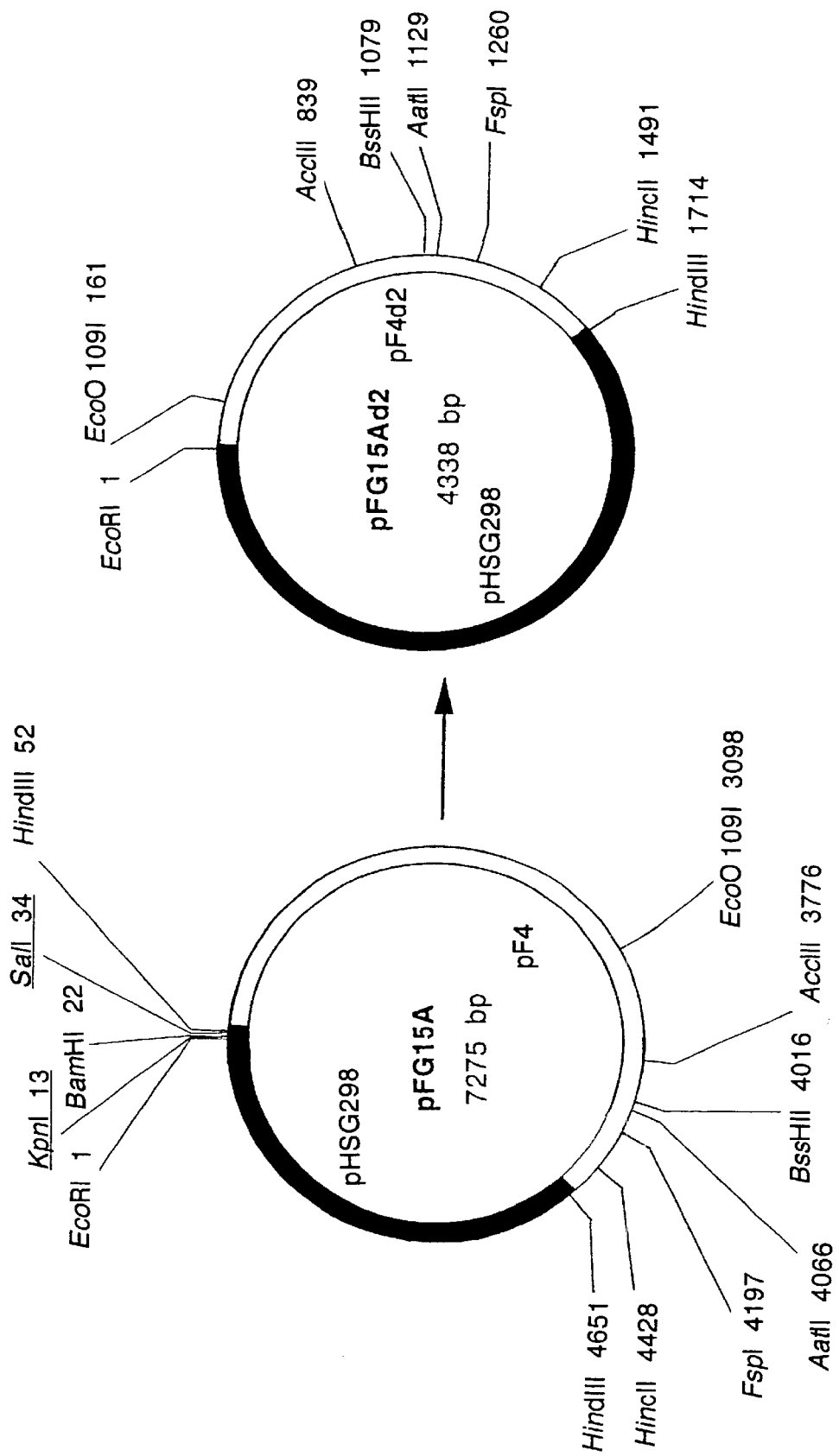
FIG. 1 shows the construction of plasmid pFG15Ad2.

Unless specifically indicated, nucleotide No. shows the nucleotide No. of the nucleotide sequence of plasmid pF4 (Sequence Listing SEQ:ID No. 1).

(1) DNA

The DNA of the present invention derived from plasmid pF4 contains a region involved in the control of autonomous replication in a bacterial cell belonging to the genus Gluconobactor. It is a DNA containing a region with or without a part of the polynucleotide region not essential for the autonomous replication. It preferably contains substantially a part or the whole of the polynucleotide of the nucleotide Nos. 2897–3969 region of Sequence Listing SEQ:ID No. 1, as the region responsible for the function of controlling autonomous replication in the genus Gluconobactor.

The DNA of the present invention includes a polynucleotide having the nucleotide sequence depicted in Sequence Listing, SEQ:ID No. 1 or the nucleotide sequence of nucleotide Nos. 2897–3969, wherein at least one nucleotide has been deleted, substituted, added or inserted, as far as the autonomous replication in the genus Gluconobactor is possible.

The plasmid pF4 from which the inventive DNA is derived, is a plasmid containing an autoreplicatable unit of *Gluconobactor oxydans* T-100 (see WO95/23220).

The bacterial cell belonging to the genus Gluconobactor, in which the inventive DNA autonomously replicates, is not particularly limited, and may be *Gluconobactor oxydans* NB6939 (see WO95/23220), *Gluconobactor oxydans* G624 (see WO95/23220), NB1707, UV10 and the like.

(2) Plasmid Vector

The plasmid vector of the present invention is derived from plasmid pF4 and contains a DNA containing a region involved in the autonomous replication in the bacterial cell belonging to the genus Gluconobactor, with or without a part of polynucleotide region not essential for the autonomous replication.

The DNA containing a region involved in the autonomous replication in the bacterial cell belonging to the genus Gluconobactor, with or without a part of polynucleotide region not essential for the autonomous replication, which is contained in the plasmid vector of the present invention, is exemplified by those mentioned above [see under (1) DNA]. By partly or entirely removing, from plasmid pF4, the nucleotide sequence region not essential for autonomous replication, pF4 can be shortened. By shortening pF4, integration of various long structural genes into an expression vector and the like when in use becomes possible.

The plasmid vector of the present invention advantageously contains an additional marker gene, such as antibiotic resistant gene, for judging the presence or otherwise of transformation.

The marker gene to be used here is exemplified by drug resistant genes such as kanamycin resistant gene, ampicillin resistant gene, chloramphenicol resistant gene and hygromycin resistant gene, auxotrophic gene and enzyme gene such as lacZ.

The plasmid vector of the present invention that contains a DNA containing a region involved in the autonomous replication in the bacterial cell belonging to the genus Gluconobactor and a DNA that controls autonomous replication in a host other than the bacterial cell belonging to the genus Gluconobactor is capable of autonomous proliferation in two different kinds of hosts, and is a so-called shuttle vector (hereinafter this plasmid vector is also referred to as the shuttle vector of the present invention).

The host other than Gluconobactor is exemplified by *Escherichia coli*, Pseudomonas, Pseudogluconobactor, Acetobacter and the like, and, from the aspects of easy handling, easy cloning and the like, *Escherichia coli* is preferably used. The DNA involved in autonomous replication in *Escherichia coli* is not particularly limited as long as it is capable of autonomous replication in *Escherichia coli*. Preferred is an autoreplicatable unit of *Escherichia coli*, which is specifically colE1, p15A, pBBR1 and the like.

The plasmid vector of the present invention may be prepared by functionally ligating, in addition to a DNA involved in the autonomous replication in the bacterial cell belonging to the genus Gluconobactor, at least one structural gene that imparts a function of expressing and producing a physiologically active substance in various hosts (hereinafter this vector is to be also referred to as recombinant expression vector of the present invention).

This expression vector advantageously contains a DNA involved in autonomous replication in a host other than a bacterial cell belonging to the genus Gluconobactor, so that autonomous replication can occur in a host other than the bacterial cell belonging to the genus Gluconobactor. This is advantageous from the aspect of cloning of expression vector.

The structural gene is not particularly limited as long as it is a gene encoding various proteins, and is exemplified by a gene encoding a desired physiologically active substance [e.g., enzymes such as L-sorbose dehydrogenase (which catalyzes conversion from L-sorbose to L-sorbosone:hereinafter to be referred to as SDH), L-sorbosone dehydrogenase (which catalyzes conversion from L-sorbosone to 2-keto-L-gulonic acid:hereinafter to be referred to as SNDH), alcohol dehydrogenase (ADH), D-sorbitol dehydrogenase (SLDH) and the like]; a gene encoding regeneration of coenzyme, carbon auxotrophicity and the like; and the like, which can be obtained by any method. For example, it may be a complementary DNA (cDNA) prepared from mRNA, a genomic DNA prepared from genomic library, a chemically synthesized DNA, a DNA obtained by amplification of RNA or DNA as a template by PCR, a DNA constructed by a suitable combination of these methods, and the like. Specific examples include SDH gene, SNDH gene and the like.

The plasmid vector of the present invention can be made into a multifunction vector by functionally ligating promoter and terminator regions and the like, in addition to the above-mentioned autonomously replicating sequence and structural gene. In particular, the promoter region that controls transcription and translation is essential for the construction of an expression vector, and a terminator region is also preferably contained.

The promoter to be used in the present invention is not particularly limited as long as it has a promoter activity that allows transcription of various structural genes in a host. More particularly, different promoters may be selected according to the kind of host and structural gene. When the structural gene is an SDH gene and/or SNDH gene, a promoter region having high transcription activity of SDH gene and/or SNDH gene, or a part thereof having a promoter activity may be used. Specific examples include promoter region of SNDH gene derived from *Gluconobactor oxydans* T-100 and a part thereof having a promoter activity. As the promoter, a promoter derived from *Escherichia coli*, such as tufB, λPL, trp, tac, lacUV5, lpp, lac, ompA, phoA, recA, rrnB and the like can be used. Preferred are tufB, λPL, trp and tac promoters. The sequences other than −35 region and −10 region of these promoters may be appropriately determined so as to be suitable for the construction of plasmid.

The recombinant expression vector of the present invention can contain two kinds of structural genes in a single vector, which may exist in a nonlimitative mode as long as the structural genes can express. The transcription and translation of the two kinds of structural genes may be controlled by individual expression systems, or the both genes may be controlled by a set of expression systems.

The expression vector having individual expression systems is exemplified by an expression vector wherein each gene is designed to undergo transcription controlled by each individual promoter. The expression vector having a set of expression systems is exemplified by an expression vector wherein each gene is so designed as to undergo continuous transcription starting from one promoter.

In the production method of 2-keto-L-gulonic acid of the present invention, a plasmid vector containing an SDH gene and/or SNDH gene as a structural gene is used. The mode of existence of these genes is free of any limitation as long as they can express SDH and SNDH. It is possible to contain two kinds of genes in a single vector or each gene may be introduced individually into an expression vector and separately introduced into a single host cell.

The terminator to be used for the expression vector of the present invention is not particularly limited as long as it corresponds to the host used for the expression of a desired structural gene. For example, trpA, rrnB and the like can be used.

(3) Transformant and Culture Thereof

The transformant of the present invention can be prepared by introducing the plasmid vector (inclusive of shuttle vector and recombinant expression vector) obtained above into a suitable host cell. The host cell is selected in accordance with the plasmid vector. For example, a shuttle vector containing a DNA that controls autonomous replication in *Escherichia coli* permits use of *Escherichia coli* as a host. When the inventive expression vector is used for transformation, the host cell is selected in accordance with the structural gene carried by the expression vector and the object thereof. For example, when the structural genes are an SDH gene and an SNDH gene, and the final product is 2-keto-L-gulonic acid, the microorganism to be used as a host produces L-sorbose from D-sorbitol at a high yield and does not have an activity to degrade 2-keto-L-gulonic acid or has a low degradation activity. Specific examples thereof include microorganisms belonging to the genera Gluconobacter and Acetobacter, such as *Gluconobactor oxydans* G624 and *Gluconobactor oxydans* NB6939 (both disclosed in WO95/23220).

The method for preparing a transformant is not particularly limited, and can be a conventional method determined as appropriate depending on the host. Specifically, competent cell method, protoplast polyethylene glycol fusion method, calcium phosphate co-precipitation method, DEAE dextran method, microinjection method, electroporation method and the like can be used. For example, when a microorganism belonging to the genus Gluconobactor or Acetobacter is used as a host, electroporation (Dower, W. J., Miller, J. F. and Ragsdale, C. W., *Nucleic Acid Res.* Vol. 16 (1988), p 6127) is advantageously used, since methods generally used for transformation can only show low transformation efficiency. This electroporation may be carried out by a method routinely used in the field of genetic engineering, or upon modification as appropriate according to the host microorganism to be transformed.

In the present invention, whether or not the host has been correctly transformed can be examined by determining a selection marker gene that the transformant has, such as a gene resistant to antibiotics (e.g., kanamycin), an auxotrophic gene, an enzyme gene such as lacZ, or a gene that can be confirmed by the transformation with an expression vector and expression of the structural gene (e.g., enzyme activity and the like).

The method for producing a physiologically active substance to be used in the present invention comprises culturing a transformant obtained transformed with an expression vector containing a structural gene encoding the physiologically active substance, and harvesting the physiologically active substance from the resultant culture. The method for producing 2-keto-L-gulonic acid in the present invention comprises culturing a transformant that expresses SDH and SNDH to produce 2-keto-L-gulonic acid and harvesting the same.

The nutrient medium to be used is a known medium suitable for the host. The medium preferably contains carbon sources, inorganic or organic nitrogen sources necessary for the growth of the host cell (transformant). Examples of the carbon source include glucose, dextrin, soluble starch, sucrose and the like; examples of the nitrogen source include ammonium salt, nitrate, amino acid, corn steep liquor, peptone, casein, meat extract, soy bean lees, potato extract and the like. If desired, other nutritious sources such as inorganic salts (e.g., potassium chloride, sodium dihydrogenphosphate, magnesium chloride), vitamins, and antibiotics (e.g., tetracycline, neomycin, kanamycin, ampicillin) may be added to the medium.

When *Escherichia coli* is a host, LB medium, M9 medium and the like are used as the medium. When a microorganism belonging to the genus Gluconobactor is used as a host, MB medium and the like can be used.

When SDH and SNDH are expressed to produce 2-keto-L-gulonic acid, the nutrient medium generally contains D-sorbitol. For example, when a microorganism belonging to the genus Gluconobactor is used as a host, a medium containing D-sorbitol, yeast extract and calcium carbonate can be used.

The cells are cultured by a method known in the field. Culture conditions such as temperature, pH of medium and culture time can be appropriately determined, so that the physiologically active substance can be produced in large amounts by the selected host cell.

When a microorganism belonging to the genus Gluconobactor is used as a host and SDH and/or SNDH are/is expressed, the pH is generally 5.5–8.5, preferably 7–7.5, culture temperature is generally 18–40° C., preferably 20–35° C., and culture time is generally 20–170 hours.

After culture, the objective physiologically active substance accumulated in the culture supernatant or transformant is extracted and purified by a known method. The culture broth is filtrated or centrifuged and isolated by a conventional method to recover cell or supernatant. When the objective product is accumulated in the cell, the recovered cell is suspended in a suitable buffer and a surfactant is added at a suitable concentration for the lysis of the membrane. When the host cell has a cell wall, a pretreatment using a lysozyme or sonication is necessary. As the surfactant, sodium dodecyl sulfate (SDS), cetyl trimethyl ammonium bromide (CTAB) and the like can be used. Because of their strong protein denaturing action, a mild non-ionic surfactant such as Triton X-100 and the like is preferably used, so that the protein can be folded while retaining biological activity. Then, the obtained crude extract is treated by an appropriate combination of conventional methods in the presence of a surfactant, where necessary, to isolate and purify the protein. When the objective product is present in the solution fraction of culture medium (e.g., the case when SDH and SNDH are expressed to produce 2-keto-L-gulonic acid), the culture medium is first subjected to centrifugation to remove precipitates (solid such as cell and the like) and the obtained solution is treated by typical methods in appropriate combination, which are conventionally used for isolation and purification of the objective product. For example, a method utilizing different solubilities, such as salting-out, solvent precipitation method and the like; a method utilizing different molecuar weights such as dialysis, ultrafiltration, gel filtration, SDS-PAGE and the like; a method utilizing charging such as ion-exchange chromatography and the like; a method utilizing specific affinity such as affinity chromatography and the like; a method utilizing different hydrophobicities such as reversed phase high performance liquid chromatography and the like; a method utilizing different isoelectric points such as isoelectric point electrophoresis and the like; and the like can be used.

Many techniques, reactions and analysis methods used in the present invention are known to those of ordinary skill in the art. In addition, enzyme, plasmid, host and the like are commercially available unless otherwise indicated.

EXAMPLES

The present invention is explained in detail in the following by way of Examples, to which the present invention is not limited.

Example 1

DNA Sequence Analysis of pF4

(1) Preparation of pF4 Plasmid

An isolated naturally occurring strain of Gluconobactor [*Gluconobactor oxydans* T-100 (FERM BP-4188, WO95/23220)] was inoculated into 10 test tubes containing 6 ml of MB medium (D-mannitol 2.5%, polypeptone 0.3%, yeast extract 0.5%, pH 6.0), and cultured at 30° C. for 18 hours in a test tube shake culture apparatus. MB medium (100 ml) was placed in each of ten 500 ml Erlenmeyer flasks, and 3 ml each of the seed culture was inoculated, which was followed by culture at 30° C. for 6 hours. The ten tubes of culture (1 litter) were centrifuged at 4° C., 6000 rpm for 10 minutes, and the obtained cells were suspended in 30 ml of P1 solution (100 $\mu$g/ml ribonuclease A, 10 mM EDTA, 50 mM Tris-HCl buffer, pH 8.0). P2 solution (30 ml, 1% SDS, 0.2 N sodium hydroxide solution) and P3 solution (30 ml, 3 M potassium acetate buffer, pH 5.5) were added, and the mixture was centrifuged at 4° C., 13000 rpm for 30 minutes. The supernatant was centrifuged again under the same conditions, and the supernatant was adsorbed to Quiagen column Tip 100 (Quagen) equilibrated with QBT solution (15% ethanol, 0.15% Triton X-100, 750 mM sodium chloride, 50 mM MOPS buffer, pH 7.0), and washed twice with 10 ml of QC solution (15% ethanol, 1 M sodium chloride, 50 mM MOPS buffer, pH 7.0), which was followed by elution with 10 ml of QF solution (15% ethanol, 1.25 M sodium chloride, 50 mM Tris-HCl buffer, pH 8.5). A 0.7-fold amount of isopropanol was added to the eluate, and the mixture was centrifuged at 4° C., 10000 rpm for 30 minutes. The precipitate was washed with 70% ethanol and dried in vacuo to give a DNA. The obtained DNA was dissolved in 150 $\mu$l of TE buffer (1 mM EDTA, 10 mM Tris-HCl buffer, pH 8.0). Using $\lambda$Hind III molecular weight marker (Boehringer Mannheim AG) as an index, these DNA solutions were migrated on 0.8% agarose gel at 100V for 30 minutes, and the single band present in the range of from 2 kb to 5 kb, which was stained with ethidium bromide, was cleaved out from the gel, placed in a dialysis tube, and migrated at 100V for 30 minutes, thereafter for 30 seconds upon reversing the flow direction of the current, and the content of the tube was transferred to an eppendorf tube. After extraction twice with water saturated phenol, the aqueous layer was washed with butanol and dehydrated repeatedly until the washing and dehydration concentrated the solution to 500 $\mu$l. 3 M sodium acetate (50 $\mu$l) and ethanol (1 ml) were added, and the mixture was left standing overnight at −20° C. The solution was centrifuged at 4° C., 14000 rpm for 30 minutes. The obtained precipitate was washed with 70% ethanol and dried in vacuo. The resulting precipitate was dissolved in TE buffer to give a plasmid solution. The pF4 plasmid (4.4 kb) derived from isolated naturally occurring strain *Gluconobactor oxydans* T-100 was obtained.

(2) Construction of Shuttle Vector pFG15A

The pF4 plasmid prepared in the above (1) and pHSG298 (Takara Shuzo) containing kanamycin resistant gene and lacZ gene containing a multicloning site, as a drug resistant plasmid containing replication origin functionable in *Escherichia coli*, were ligated to give a combined plasmid pFG15A containing a kanamycin resistant gene.

pHSG298 was partially cleaved with restriction enzyme Hind III (Nippon gene, Japan), subjected to alkaline phosphatase treatment and ligated with pF4 cleaved with Hind III using T4DNA ligase to give pFG15A.

The DNA sequence of the pF4 part of pFG15A was determined using a 373A DNA sequencer (Applied Biosystems, USA) by dideoxy termination method using REV Y or UNI 40 primer shown below, which is based on the DNA sequence of pHSG298, according to the attached protocol.

REV Y 5'>GATAACAATTTCACACAGG<3' (Sequence Listing SEQ:ID No. 2)

UNI 40 5'>GTTTTCCCAGTCACGAC<3' (Sequence Listing SEQ:ID No. 3)

Based on the DNA sequence identified by the first sequence analysis, various primers were synthesized and subjected to DNA sequence analysis. The primers used were synthesized as follows.

Each oligonucleotide listed in Table 1 and Table 2 was synthesized by phospho amidite method using DNA synthesizer model 392 (Applied Biosystems, USA). The synthesized oligonucleotide was liberated from CPG polymer with 28% aqueous ammonia, followed by heating at 60° C. for 9 hours to remove all protective groups. The reaction mixture was evaporated in vacuo, and the residue was dissolved in 200 $\mu$l of TE buffer. The obtained solution was washed once with ether and precipitated with ethanol. The oligonucleotide obtained by precipitation was used as a primer for DNA sequence analysis. The results are shown in Table 1 and Table 2.

TABLE 1

| Primer | Sequence | | Location |
|---|---|---|---|
| 1R | 5'>CGCGACCTTGCGCAG<3' | (SEQ:ID No. 4) | 4306–4320 |
| 2R | 5'>GCCTGCTCATGACGC<3' | (SEQ:ID No. 5) | 276–90 |
| 3R | 5'>CGATCTGAACGCTTG<3' | (SEQ:ID No. 6) | 4107–4121 |

TABLE 1-continued

| Primer | Sequence | | Location |
|---|---|---|---|
| 4R | 5'>CAAGCTTCGCAAACG<3' | (SEQ:ID No. 7) | 525–539 |
| 5RY | 5'>CTGCACACCTATCGCC<3' | (SEQ:ID No. 8) | 3977–3992 |
| 6RY | 5'>TGACCGCAACCAGCG<3' | (SEQ:ID No. 9) | 772–786 |
| 7RY | 5'>AAGGCTGAACTCGAAGC<3' | (SEQ:ID No. 10) | 4243–4259 |
| 8RY | 5'>ATCCCGCACGATGAGG<3' | (SEQ:ID No. 11) | 481–496 |
| 9RY | 5'>ACGAGCGCTCGATACC<3' | (SEQ:ID No. 12) | 3622–3637 |
| 10RY | 5'>ACGAAAGGAGCTGCATG<3' | (SEQ:ID No. 13) | 347–363 |
| 11RY | 5'>GATGTGGTGAAGACTCG<3' | (SEQ:ID No. 14) | 3397–3413 |
| 12RY | 5'>TCAGTGAGCGGGTTCC<3' | (SEQ:ID No. 15) | 706–721 |
| 13RY | 5'>GAAGGCGTCTGGTGTG<3' | (SEQ:ID No. 16) | 2984–2999 |
| 14RY | 5'>CGGGGTTGAATTTTGCC<3' | (SEQ:ID No. 17) | 1259–1275 |
| 15RY | 5'>CACACCACGACTCTGC<3' | (SEQ:ID No. 18) | 985–1000 |
| 16RY | 5'>CAGGCTGATCCAGTCC<3' | (SEQ:ID No. 19) | 1738–1753 |
| 17RY | 5'>GCGGCTCTGGCATGG<3' | (SEQ:ID No. 20) | 2616–2630 |
| 18RY | 5'>CGTACTGACTTGATACAAG<3' | (SEQ:ID No. 21) | 2211–2229 |

TABLE 2

| Primer | Sequence | | Location |
|---|---|---|---|
| 1U | 5'>CTGCGCAAGGTCGCG<3' | (SEQ:ID No. 22) | 4306–4320 (Reverse) |
| 2U | 5'>GCGTCATGAGCAGGC<3' | (SEQ:ID No. 23) | 276–290 (Reverse) |
| 3U | 5'>CAAGCGTTCAGATCG<3' | (SEQ:ID No. 24) | 4107–4121 (Reverse) |
| 4U | 5'>CGTTTGCGAAGCTTG<3' | (SEQ:ID No. 25) | 525–539 (Reverse) |
| 5UY | 5'>GAGATGGCTGGCAAGG<3' | (SEQ:ID No. 26) | 3893–3908 (Reverse) |
| 6UY | 5'>TGGCCTGAAGCCATGC<3' | (SEQ:ID No. 27) | 430–445 (Reverse) |
| 7UY | 5'>GATGCAGCGCGAGGG<3' | (SEQ:ID No. 28) | 3505–3519 (Reverse) |
| 8UY | 5'>TCATGCAGCTCCTTTCG<3' | (SEQ:ID No. 29) | 348–364 (Reverse) |
| 9UY | 5'>TCACCAGCTATGAGGC<3' | (SEQ:ID No. 30) | 3205–3220 (Reverse) |
| 10UY | 5'>GCCGATACCACATCCG<3' | (SEQ:ID No. 31) | 642–657 (Reverse) |
| 11UY | 5'>CGAGTCTTCACCACATC<3' | (SEQ:ID No. 32) | 3397–3413 (Reverse) |
| 12UY | 5'>GATGGAGGCTGTAGGC<3' | (SEQ:ID No. 33) | 1204–1219 (Reverse) |
| 13UY | 5'>CTCTGGTGCTGCAAGG<3' | (SEQ:ID No. 34) | 2937–2952 (Reverse) |
| 14UY | 5'>GAACGGTTCGGAGAGC<3' | (SEQ:ID No. 35) | 1695–1710 (Reverse) |
| 15UY | 5'>CCACACCAGACGCCTTC<3' | (SEQ:ID No. 36) | 2984–3000 (Reverse) |
| 16UY | 5'>TCGATTACGCTGGCAGC<3' | (SEQ:ID No. 37) | 2095–2111 (Reverse) |
| 17UY | 5'>AGGTGGACCATCTGGC<3' | (SEQ:ID No. 38) | 2687–2702 (Reverse) |
| 18UY | 5'>ATCCGCAAAAGCAGACC<3' | (SEQ:ID No. 39) | 1428–1444 (Reverse) |
| 19UY | 5'>GTTTCCAGTCAAAACGCC<3' | (SEQ:ID No. 40) | 2859–2876 (Reverse) |
| 20UY | 5'>CGGGTCCTGTGGACC<3' | (SEQ:ID No. 41) | 3040–3054 (Reverse) |

As a result of the analysis, the sequence of 4599 base pairs of the pF4 part was determined. The sequence of pF4 is shown in Sequence Listing SEQ:ID No. 1.

Example 2

Preparation of Deficient pFG15A Plasmid-1

Using the restriction enzymes Kpn I and Sal I, plasmid pFG15A prepared in Example 1 was digested, extracted with phenol/chloroform and chloroform, and purified by ethanol precipitation. The thus-purified DNA (ca. 7.2 kb) was treated using a kilo-sequencing Deletion Kit (Takara Shuzo, Japan) according to the attached protocol to give several deficient plasmids. To be specific, DNA was made deficient from Sal I digestion end by Exonuclease III and Mung Bean Nuclease and blunted with Klenow Fragment. The blunted DNA was ligated with DNA ligase. *Escherichia coli* DH10B was transformed with the obtained DNA by the electroporation method. Three kinds of plasmids having suitable size were obtained from the transformed *Escherichia coli*, and respectively named pFG15Ad1, pFG15Ad2 and pFG15Ad3. As an example, construction of pFG15Ad2 is schematically shown in FIG. 1.

The obtained three kinds of plasmids were introduced into *Gluconobactor oxydans* NB6939 [strain disclosed in Example 17 of WO95/23220; Gluconobactor strain transformed with expression vector pSDH155 (SDH gene and SNDH gene ligated to shuttle vector pFG15A) and treated with novobiocin to completely remove pSDH155] by electroporation method (Dower, W. J., Miller, J. F. and Ragsdale, C. W., *Nucleic Acid Res.* Vol. 16 (198), p 6127) in the following manner.

First, competent cell of *Gluconobactor oxydans* NB6939 was prepared. *Gluconobactor oxydans* NB6939 was inoculated into 500 ml Erlenmeyer flask containing 100 ml of MB medium (D-mannitol 2.5%, polypeptone 0.3%, yeast extract 0.5%, pH 6.0), and cultured at 25° C. for about 20 hours. After confirming that the absorbance of the culture medium at 570 nm was in the range of from 0.6 to 1.2, the cells were collected by centrifugation at 4° C., 6000 rpm for 10 minutes. The competent cells were collected by washing the above-mentioned centrifuged cells with 10% glycerol and again centrifuging at 4° C., 6000 rpm for 10 minutes, which was followed by preparation of a suspension of $10^{10}$ cells/ml under microscope. The three kinds of plasmids (pFG15Ad1, pFG15Ad2 and pFG15Ad3) obtained above were isolated and purified according to the plasmid preparation method shown in Example 1(1) and diluted with TE buffer to give a DNA 4 mg/ml solution for use. This plasmid solution (1

μl) was added to the competent cell suspension (160 μl), mixed, and this suspension (60 μl) was placed in cuvette of Gene Pulser (Bio Rad). Electroporation was carried out at cuvette width 0.1 cm, resistance 200Ω, voltage 1.8 KV and capacity 25 μF. MB medium (1 ml) was added to the transformation solution in the cuvette to give a suspension and the entire amount thereof was transferred into a 15 ml Corning tube, which was followed by rotary (80 rpm) incubation in an incubator warm water tank at 30° C. for 2 hours. The suspension was plated on MB agar plate containing kanamycin (100 μg/ml) and the colonies grown were counted. As a result, it was found that *Gluconobactor oxydans* NB6939 was transformed with pFG15Ad1 and pFG15Ad2 but was not transformed with pFG15Ad3.

The DNA sequences of the pF4 part of pFG15Ad1, pFG15Ad2 and pFG15Ad3 were analyzed in the same manner as in Example 1 with 373A DNA sequencer by dideoxy termination method using REV Y or UNI 40 primer. The pF4 parts (shortened) of pFG15Ad1, pFG15Ad2 and pFG15Ad3 are referred to as pF4d1, pF4d2 and pF4d3, respectively, in this specification. The results are shown in Table 3.

TABLE 3

| vector | transformation | nucleotide sequence of pF4 part |
|---|---|---|
| pFG15A | possible | 1–4599 |
| PFG15Ad1 | possible | 2375–4599 |
| pFG15Ad2 | possible | 2897–4599 |
| pFG15Ad3 | impossible | 3333–4599 |

The results suggest that the nucleotide sequence of 1–2896 of pF4 is not necessary for the transformation of bacterial cell belonging to the genus Gluconobactor.

Example 3

Preparation of Deficient pFG15A Plasmid-2

Figure 2:
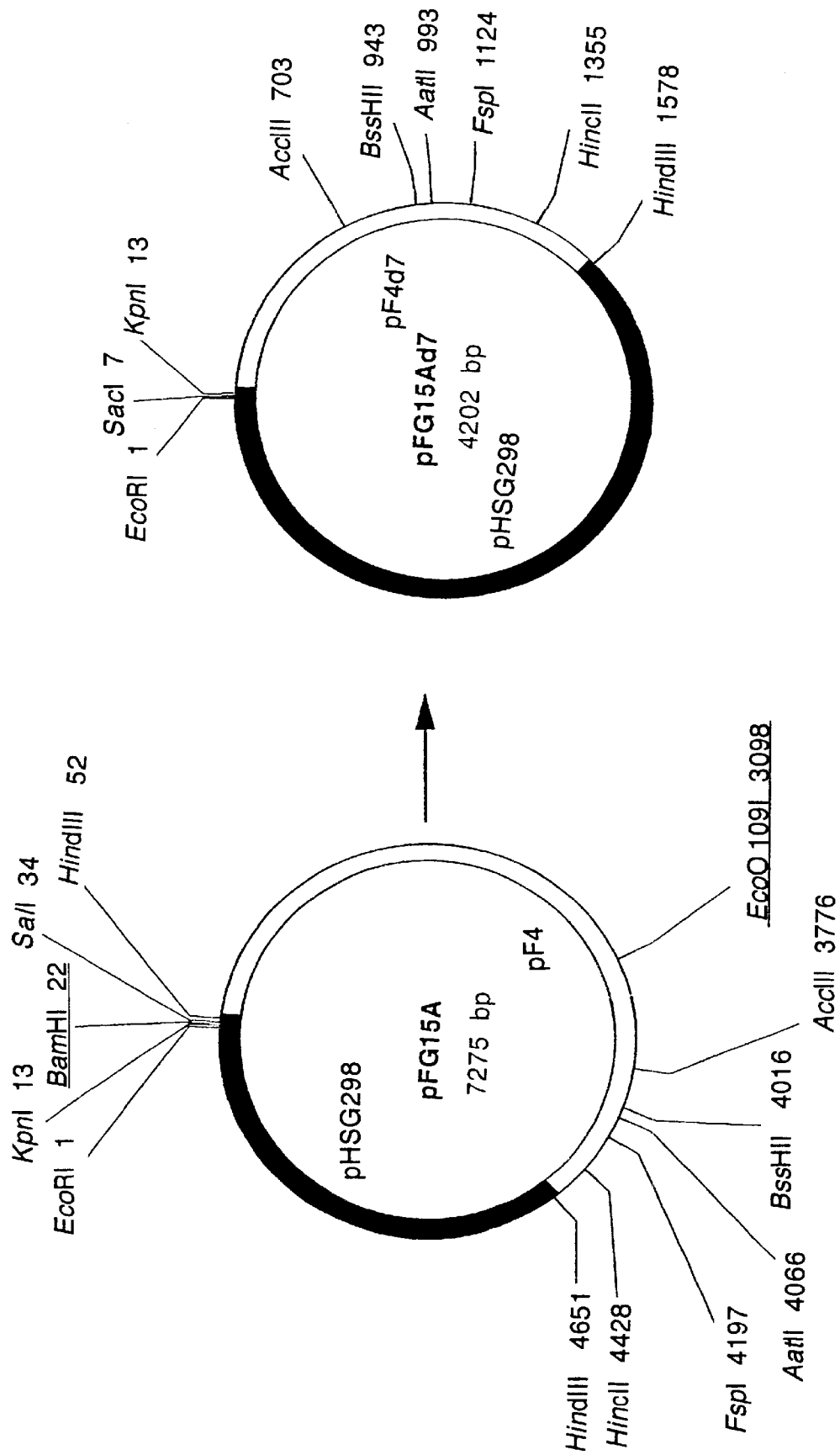
FIG. 2 shows the construction of plasmid pFG15Ad7.

Using the restriction enzymes EcoO109 I and BamH I, plasmid pFG15A (mentioned above) was digested, and both digestion fragments were blunted with Klenow Fragment. The blunted DNA fragment (ca. 4.2 kb) was isolated by agarose gel-electrophoresis and ligated with DNA ligase. *Escherichia coli* DH10B was transformed with the ligated DNA by the electroporation method. Plasmid pFG15Ad7 was obtained from the transformed *Escherichia coli* (FIG. 2).

The obtained plasmid pFG15Ad7 was introduced into Gluconobactor oxydans NB6939 according to the method described in Example 2. Gluconobactor was not transformed with pFG15Ad7. According to Example 1, the DNA sequence of the pF4 part of pFG15Ad7 was analyzed. In the present specification, the pF4 part (shortened) of pFG15Ad7 is referred to as pF4d7. The results are shown in Table 4.

TABLE 4

| vector | transformation | nucleotide sequence of pF4 part |
|---|---|---|
| pFG15Ad7 | impossible | 3052–4599 |

Example 4

Preparation of Deficient pFG15A Plasmid-3

The plasmid pFG15Ad2 prepared in Example 2 was digested with restriction enzymes EcoR I and Hinc II, and the digested ca. 1.5 kb DNA fragment was isolated by agarose gel-electrophoresis. Plasmid pHSG298 was digested with restriction enzymes EcoR I and Hinc II, and the digested ca. 2.6 kb DNA fragment was isolated by agarose gel-electrophoresis. The isolated both DNA fragments were ligated with T4 DNA ligase, and *Escherichia coli* DH10B was transformed with the obtained DNA by electroporation method. Plasmid pFG15Ad9 was obtained from the transformed *Escherichia coli*.

Figure 3:
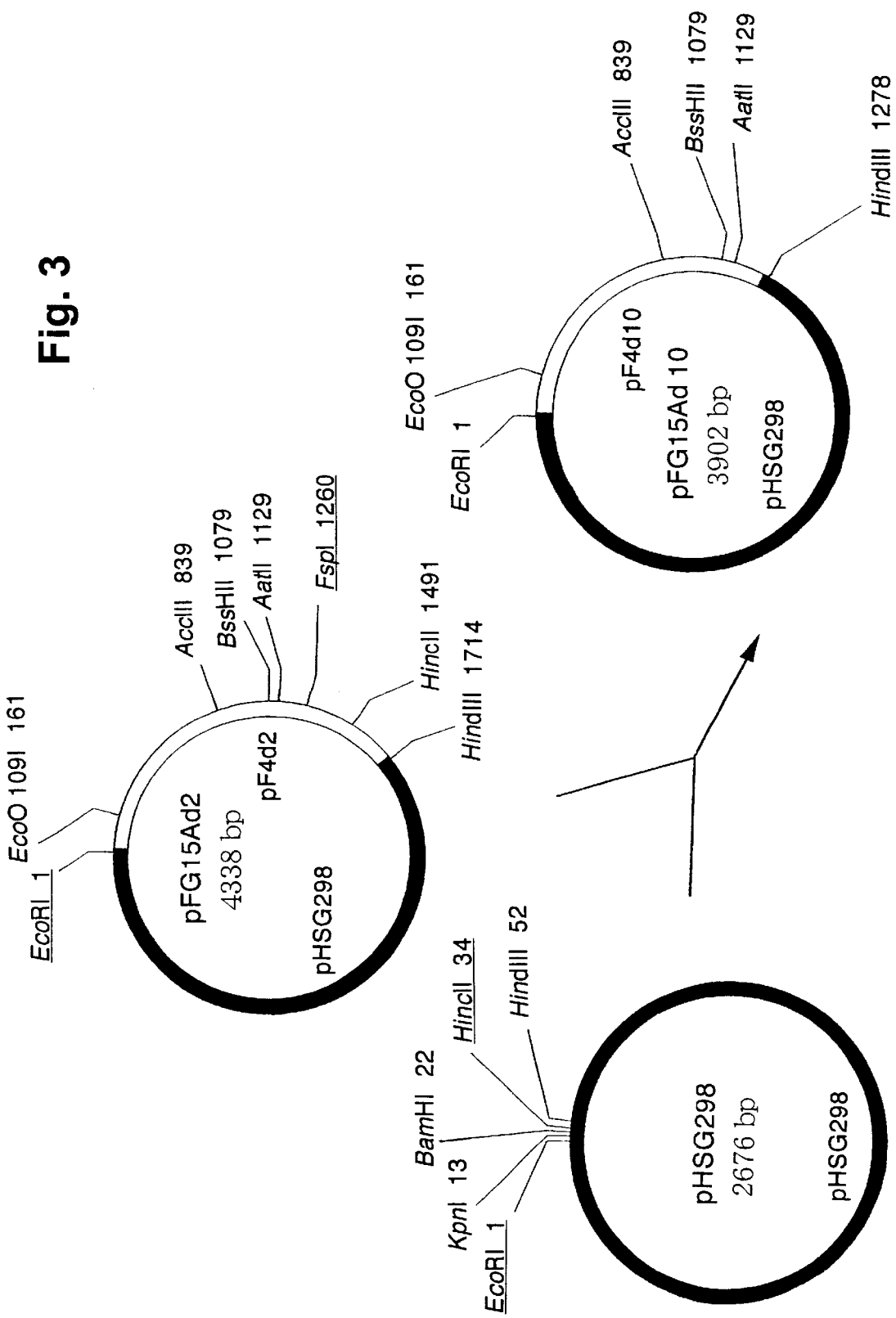
FIG. 3 shows the construction of plasmid pFG15Ad10.

The plasmid pFG15Ad2 prepared in Example 2 was digested with restriction enzymes Fsp I and EcoR I, and the digested ca. 1.3 kb DNA fragment was isolated by agarose gel-electrophoresis. Plasmid pHSG298 was digested with restriction enzymes EcoR I and Hinc II, and the digested ca. 2.6 kb DNA fragment was isolated by agarose gel-electrophoresis. The isolated both DNA fragments were ligated with T4 DNA ligase, and *Escherichia coli* DH10B was transformed with the obtained DNA by electroporation method. Plasmid pFG15Ad10 was obtained from the transformed *Escherichia coli* (FIG. 3).

The obtained plasmids pFG15Ad9 and pFG15Ad10 were introduced into *Gluconobactor oxydans* NB6939 according to the method described in Example 2. *Gluconobactor oxydans* NB6939 could be transformed with pFG15Ad9 and pFG15Ad10. The DNA sequences of the pF4 part of pFG15Ad9 and pFG15Ad10 were analyzed in the same manner as in Example 1. The pF4 parts (shortened) of pFG15Ad9 and pFG15Ad10 are referred to as pF4d9 and pF4d10, respectively, in this specification. The results are shown in Table 5.

TABLE 5

| vector | transformation | nucleotide sequence of pF4 part |
|---|---|---|
| pFG15Ad9 | possible | 2897–4379 |
| pFG15Ad10 | possible | 2897–4148 |

The results suggest that the region of nucleotide Nos. 4149–4599 of pF4 is not necessary for the transformation of bacterial cell belonging to the genus Gluconobactor.

Example 5

Preparation of Deficient pFG15A Plasmid-4

Using the restriction enzymes Aat II and Pst I, plasmid pFG15Ad10 prepared in Example 4 was digested, and the digested ca. 3.8 kb DNA fragment was isolated by agarose gel-electrophoresis. The isolated DNA fragment was treated and blunted using DNA Blunting Kit (Takara Shuzo) according to the attached protocol. The blunted DNA fragment was ligated with DNA ligase and *Escherichia coli* DH10B was transformed by electroporation. Plasmid pFG15Ad12 was obtained from the transformed *Escherichia coli*.

Figure 4:
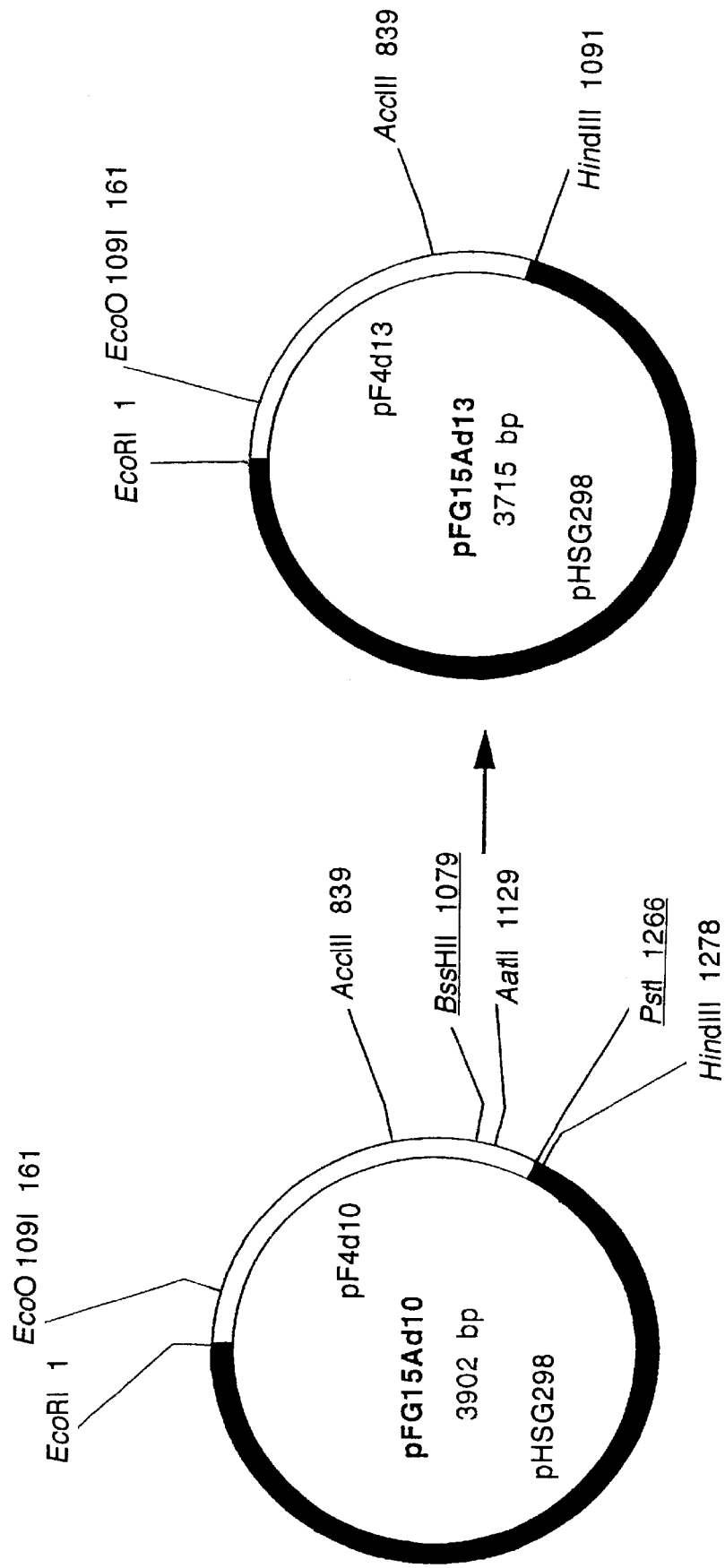
FIG. 4 shows the construction of plasmid pFG15Ad13.

Plasmid pFG15Ad10 prepared in Example 4 was digested with restriction enzymes BssH II and Pst I and the digested ca. 3.7 kb DNA fragment was isolated by agarose gel-electrophoresis. The isolated DNA fragment was treated and blunted using DNA Blunting Kit (Takara Shuzo, Japan) according to the attached protocol. The blunted DNA fragment was ligated with DNA ligase and *Escherichia coli* DH10B was transformed by electroporation. Plasmid pFG15Ad13 was obtained from the transformed *Escherichia coli* (FIG. 4). pFG15Ad10 prepared in Example 4 was digested with restriction enzymes Acc III and Pst I. The digested ca. 3.5 kb DNA fragment was isolated by agarose gel-electrophoresis. The isolated DNA fragment was treated and blunted using DNA Blunting Kit (Takara Shuzo, Japan) according to the attached protocol. The blunted DNA fragment was ligated with DNA ligase and *Escherichia coli* DH10B was transformed by electroporation method. Plasmid pFG15Ad14 was obtained from the transformed *Escherichia coli*.

The obtained plasmids (pFG15Ad12, pFG15Ad13 and pFG15Ad14) were introduced into *Gluconobactor oxydans* NB6939 according to the method described in Example 2. Gluconobactor was transformed with pFG15Ad12 and pFG15Ad13 but was not transformed with pFG15Ad14. The DNA sequence of the pF4 part of pFG15Ad12, pFG15Ad13 and pFG15Ad14 was analyzed according to Example 1. In this specification, the pF4 parts (shortened) of pFG15Ad12, pFG15Ad13 and pFG15Ad14 are referred to as pF4d12, pF4d13 and pF4d14, respectively. The results are shown in Table 6.

TABLE 6

| vector | transtormation | nucleotide sequence of pF4 part |
|---|---|---|
| pFG15Ad12 | possible | 2897–4015 |
| pFG15Ad13 | possible | 2897–3969 |
| pFG15Ad14 | impossible | 2897–3729 |

Gluconobactor could be transformed with pFG15Ad12 and pFG15Ad13 but could not be transformed with pFG15Ad14, by which it was clarified that the 630 bp nucleotide sequence of 3970–4599 was not necessary for the transformation of becterial cell belonging to the genus Gluconobactor. Thus, the nucleotide sequence of pF4 necessary for the transformation of becterial cell belonging to the genus Gluconobactor exists in the region from $2897^{th}$ to $3969^{th}$ nucleotides.

Example 6

Construction of Expression Vector pSDH-tufB1-Eco

An oligo DNA (5'>CGGAATTCCGTGCA<3'; Sequence Listing SEQ:ID No. 42) that was converted from restriction enzyme Pst I site to restriction enzyme EcoR I site was synthesized using DNA synthesizer model 392 (Applied Biosystems Inc., USA). The 5' terminal of the synthesized DNA was phospholylated using T4 polynucleotide kinase (Takara Shuzo, Japan).

Figure 5:
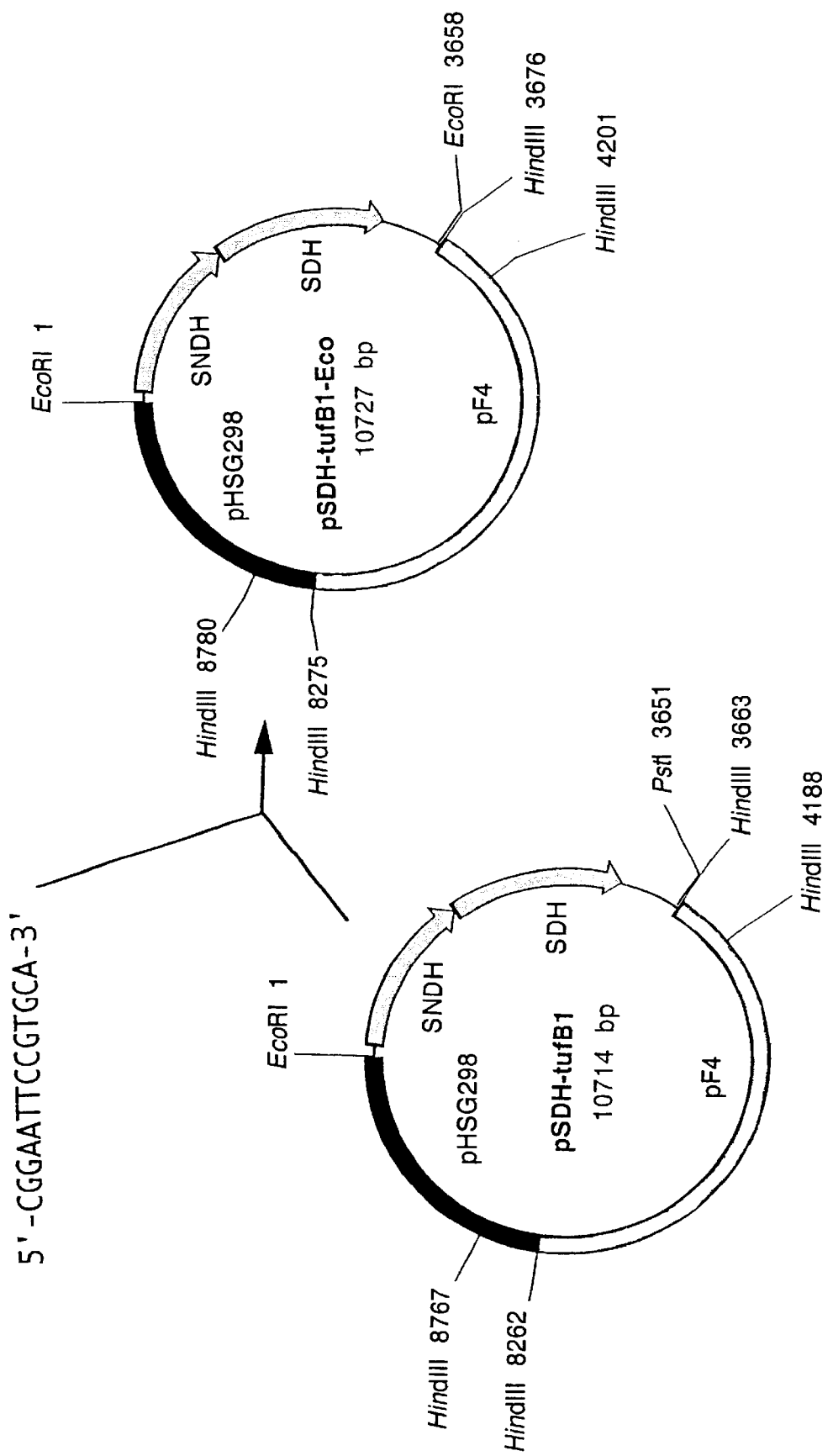
FIG. 5 shows the construction of expression vector pSDH-tufB1-Eco.

On the other hand, plasmid pSDH-tufB1 (expression vector containing part of SNDH gene and SDH gene as structural gene and tufB promoter which is an *Escherichia coli* promoter as promoter, and part of pF4, see WO95/23220) was digested with restriction enzyme Pst I, ligated with the above-mentioned phospholyated oligo DNA using T4 DNA ligase, and *Escherichia coli* DH10B was transformed with the obtained plasmid by electroporation method. The expression vector pSDH-tufB1-Eco (FIG. 5), wherein restriction enzyme Pst I site was converted to restriction enzyme EcoR I site, from the transformed *Escherichia coli*.

Example 7

Figure 6:
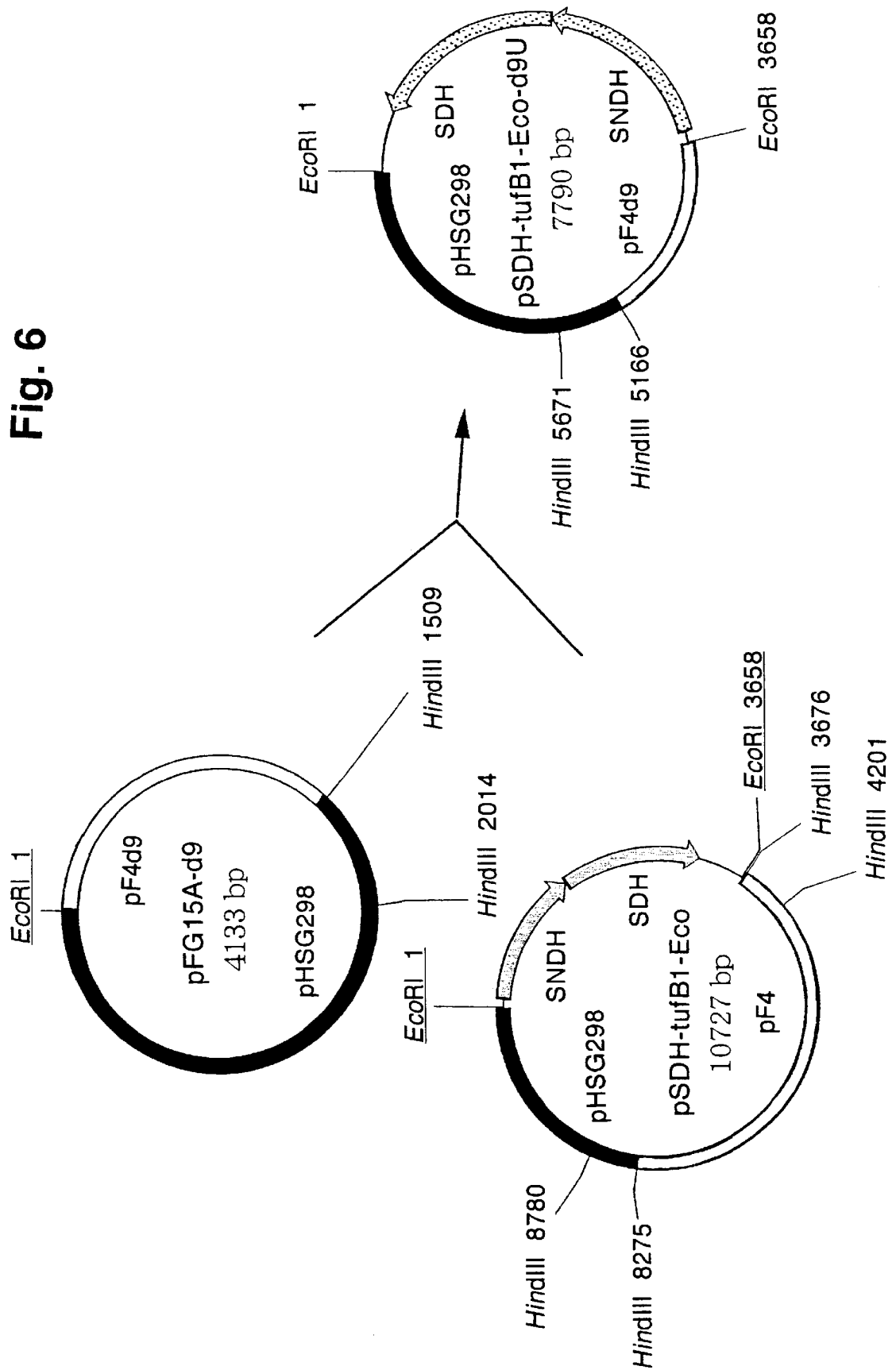
FIG. 6 shows the construction of expression vector pSDH-tufB1-Eco-d9U.

Insertion of SNDH and SDH Gene into Deficient Shuttle Vector (1) The expression vector pSDH-tufB1-Eco prepared in Example 6 was digested using restriction enzyme EcoR I and ca. 3.65 kb DNA fragment containing SNDH and SDH gene was isolated by agarose gel-electrophoresis. The isolated ca. 3.65 kb DNA fragment and pFG15Ad9 (prepared in Example 4) digested with EcoRI was ligated using T4 DNA ligase, and *Escherichia coli* DH10B was transformed by electroporation with the plasmid obtained above. An expression vector pSDH-tufB1-Eco-d9U (FIG. 6), wherein SNDH and SDH gene was inserted counterclockwise, was obtained from the transformed *Escherichia coli*. At the same time, an expression vector pSDH-tufB1-Eco-d9UW, wherein SNDH and SDH gene were sequentially and twice inserted counterclockwise, was obtained.

Figure 7:
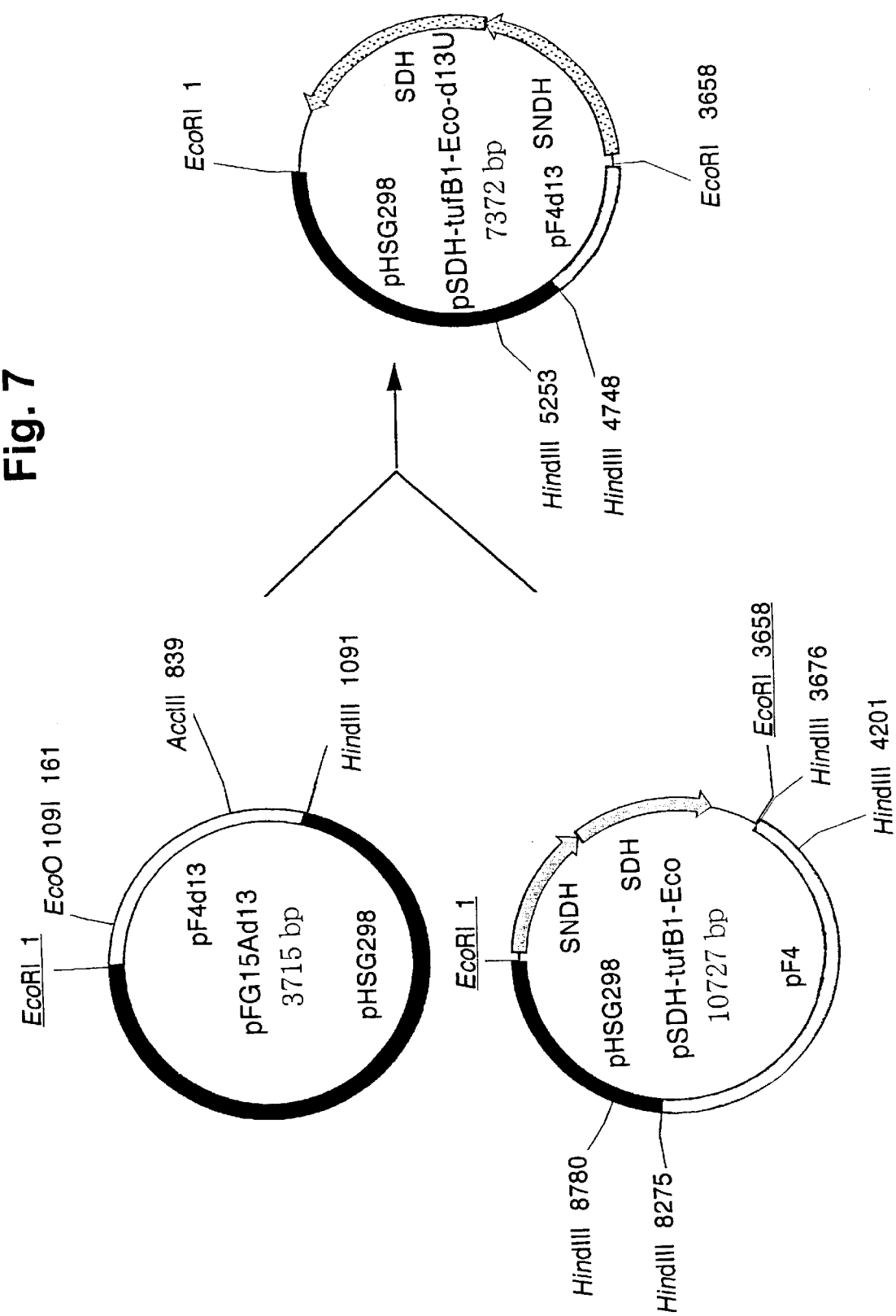
FIG. 7 shows the construction of expression vector pSDH-tufB1-Eco-d13U.

(2) The expression vector pSDH-tufB1-Eco prepared in Example 6 was digested using restriction enzyme EcoR I and ca. 3.65 kb DNA fragment containing SNDH and SDH gene was isolated by agarose gel-electrophoresis. The isolated ca. 3.65 kb DNA fragment and pFG15Ad13 (prepared in Example 5) digested with EcoR I were ligated using T4 DNA ligase, and *Escherichia coli* DH10B was transformed by electroporation method with the plasmid obtained above. An expression vector pSDH-tufB1-Eco-d13U (FIG. 7), wherein SNDH and SDH gene were inserted counterclockwise, was obtained from the transformed *Escherichia coli*. At the same time, an expression vector pSDH-tufB1-Eco-d13UW, wherein SNDH and SDH gene were sequentially and twice inserted counterclockwise, was obtained.

Example 8

Production of 2-Keto-L-gulonic Acid (1) Obtainment of Mutant Strain

*Gluconobactor oxydans* NB6939 was transformed with pSDH-tufB1. The obtained transformant strain NB6939/pSDH-tufB1 was mutated using nitrosoguanidine to give mutant 2-keto-L-gulonic acid producing strain *Gluconobactor oxydans* HS17-15 strain. The HS17-15 strain was inoculated into a test tube containing 6 ml of a medium containing glucose (2.5%), polypeptone (1.0%), yeast extract (0.5%), calcium carbonate (0.5%) and kanamycin (50 µg/ml), and was cultured in a test tube shaker at 30° C. for 18 hours to give a seed culture. The seed culture (1 ml) was inoculated into a 100 ml Erlenmeyer flask containing 20 ml of MB medium containing novobiocin (0.5 µg/ml). The flask was cultured in rotary shaker (250 rpm) at 30° C. for 24 hours and subcultured 5 passages in the same medium. This culture medium was spread on a kanamycin free MB agar plate and cultured at 30° C. for 2 days. The formed colony was replicated onto kanamycin free MB agar plate and MB agar plate supplemented with kanamycin 50 µg/ml and the strain that lost expression vector pSDH-tufB1 was selected. As a result, an NB1707 strain wherein expression vector pSDH-tufB1 alone was removed without affecting the productivity of L-sorbose from D-sorbitol was obtained.

(2) Transformation and 2-Keto-L-gulonic Acid Production of Transformant Cell Line In the same manner as in Example 2, *Gluconobactor oxydans* NB1707 obtained above was transformed with pSDH-tufB1-Eco-d9U, pSDH-tufB1-Eco-d9UW, pSDH-tufB1-Eco-d13U or pSDH-tufB1-Eco-d13UW, which were prepared in Example 7. Each recombinant was seed cultured by the method described in the above (1), and this seed culture (0.3 ml) was each inoculated into 100 ml Erlenmeyer flask containing 10 ml of medium containing D-sorbitol (15%), yeast extract (0.5%) and calcium carbonate (2.0%), and cultured in rotary (250 rpm) shaker at 30° C. for 5 days. The expressed SDH activity and SNDH activity were examined by measuring the amount of the final reaction product, 2-keto-L-gulonic acid, using HPLC. D-sorbitol was oxidized by the host, bacterial cell belonging to the genus Gluconobactor, into L-sorbose, and converted to 2-keto-L-gulonic acid through L-sorbosone by the both enzymes expressed in this bacterial cell.

The culture medium was centrifuged at 4° C., 6000 rpm for 10 minutes. The obtained supernatant was analyzed by HPLC (column Capcellpak NH$_2$; 4.6 m inner diameter×250 mm, Shiseido). As the mobile phase, 20 mM sodium phosphate buffer (pH 3.0) containing 30% acetonitrile was used at a flow rate of 1.2 ml/min. The detection was based on ultraviolet absorption at 210 nm. The results are shown in Table 7.

TABLE 7

| Strain/Expression vector | Direction of gene insertion | Number of gene | Amount of 2KLGA (mg/ml) |
|---|---|---|---|
| NB1707/pSDH-tufB1 | (clockwise) | 1 | 87 |
| NB1707/pSDH-tufB1-Eco-d9U | (counterclockwise) | 1 | 88 |
| NB1707/pSDH-tufB1-Eco-d9UW | (counterclockwise) | 2 | 87 |
| NB1707/pSDH-tufB1-Eco-d13U | (counterclockwise) | 1 | 78 |
| NB1707/pSDH-tufB1-Eco-d13UW | (counterclockwise) | 2 or above | 80 |

As a result, the expression vector containing the region necessary for the transformation of Gluconobactor, wherein pF4d9 and pF4d13 (shortened pF4 part) were incorporated instead of pF4, showed the same amount of 2-keto-L-gulonic acid as in the case of pF4 (not shortened).

Industrial Applicability

The region of the sequence of plasmid pF4 derived from the genus Gluconobactor essential for the replication in a bacterial cell belonging to the genus Gluconobactor was specified, whereby a shortened pF4 free of the region not essential for the replication and derived from plasmid pF4 could be obtained. When a plasmid vector is constructed, the use of such shortened pF4 results in a shorter vector, which in turn enables insertion of many or long structural gene, whereby a multitude of functions can be imparted. Moreover, transformation with a shuttle vector containing many structural genes results in a transformant having many capabilities.

The full length nucleotide sequence of plasmid pF4 derived from Gluconobactor was provided, whereby insertion of structural gene into an expression vector can be facilitated.

This application is based on application No. 303395/1997 filed in Japan, the content of which is incorporated hereinto by reference.

All of the references cited herein, including publications, patents and patent applications are hereby incorporated in their entireties by reference, to the same extent as if each reference was set forth in its entirety herein.

SEQUENCE LISTING FREE TEXT

SEQ: ID No. 2 Oligonucleotide designed to act as reverse sequencing primer.
SEQ: ID No. 3 Oligonucleotide designed to act as universal sequencing primer.
SEQ: ID No. 4 Oligonucleotide designed to act as reverse sequencing primer.
SEQ: ID No. 5 Oligonucleotide designed to act as reverse sequencing primer.
SEQ: ID No. 6 Oligonucleotide designed to act as reverse sequencing primer.
SEQ: ID No. 7 Oligonucleotide designed to act as reverse sequencing primer.
SEQ: ID No. 8 Oligonucleotide designed to act as reverse sequencing primer.
SEQ: ID No. 9 Oligonucleotide designed to act as reverse sequencing primer.
SEQ: ID No. 10 Oligonucleotide designed to act as reverse sequencing primer.
SEQ: ID No. 11 Oligonucleotide designed to act as reverse sequencing primer.
SEQ: ID No. 12 Oligonucleotide designed to act as reverse sequencing primer.
SEQ: ID No. 13 Oligonucleotide designed to act as reverse sequencing primer.
SEQ: ID No. 14 Oligonucleotide designed to act as reverse sequencing primer.
SEQ: ID No. 15 Oligonucleotide designed to act as reverse sequencing primer.
SEQ: ID No. 16 Oligonucleotide designed to act as reverse sequencing primer.
SEQ: ID No. 17 Oligonucleotide designed to act as reverse sequencing primer.
SEQ: ID No. 18 Oligonucleotide designed to act as reverse sequencing primer.
SEQ: ID No. 19 Oligonucleotide designed to act as reverse sequencing primer.
SEQ: ID No. 20 Oligonucleotide designed to act as reverse sequencing primer.
SEQ: ID No. 21 Oligonucleotide designed to act as reverse sequencing primer.
SEQ: ID No. 22 Oligonucleotide designed to act as universal sequencing primer.
SEQ: ID No. 23 Oligonucleotide designed to act as universal sequencing primer.
SEQ: ID No. 24 Oligonucleotide designed to act as universal sequencing primer.
SEQ: ID No. 25 Oligonucleotide designed to act as universal sequencing primer.
SEQ: ID No. 26 Oligonucleotide designed to act as universal sequencing primer.
SEQ: ID No. 27 oligonucleotide designed to act as universal sequencing primer.
SEQ: ID No. 28 Oligonucleotide designed to act as universal sequencing primer.
SEQ: ID No. 29 Oligonucleotide designed to act as universal sequencing primer.
SEQ: ID No. 30 Oligonucleotide designed to act as universal sequencing primer.
SEQ: ID No. 31 Oligonucleotide designed to act as universal sequencing primer.
SEQ: ID No. 32 Oligonucleotide designed to act as universal sequencing primer.
SEQ: ID No. 33 Oligonucleotide designed to act as universal sequencing primer.
SEQ: ID No. 34 Oligonucleotide designed to act as universal sequencing primer.
SEQ: ID No. 35 Oligonucleotide designed to act as universal sequencing primer.
SEQ: ID No. 36 Oligonucleotide designed to act as universal sequencing primer.
SEQ: ID No. 37 Oligonucleotide designed to act as universal sequencing primer.
SEQ: ID No. 38 Oligonucleotide designed to act as universal sequencing primer.

SEQ: ID No. 39 Oligonucleotide designed to act as universal sequencing primer.
SEQ: ID No. 40 Oligonucleotide designed to act as universal sequencing primer.
SEQ: ID No. 41 Oligonucleotide designed to act as universal sequencing primer.
SEQ: ID No. 42 Oligonucleotide designed for use in changing restriction site from Pst I site to EcoR I site.

What is claimed is:

1. An isolated or purified DNA consisting of a polynucleotide fragment of pF4 beginning at a nucleotide in the range 2375–2897 of SEQ ID NO: 1 and ending at a nucleotide in the range 3969–4599 of SEQ ID NO: 1 and optionally one or more nucleotide sequences exogeneous to plasmid pF4.

2. The DNA of claim 1, consisting of nucleotides 2375–4599 of SEQ ID NO: 1 and optionally one or more nucleotide sequences exogeneous to plasmid pF4.

3. The DNA of claim 1 consisting of residues 2897–4599 of SEQ ID NO: 1 and optionally one or more nucleotide sequences exogeneous to plasmid pF4.

4. The DNA of claim 1 consisting of nucleotides 2897–4379 of SEQ ID NO: 1 and optionally one or more nucleotide sequences exogeneous to plasmid pF4.

5. The DNA of claim 1 consisting of nucleotides 2897–4148 of SEQ ID NO: 1 and optionally one or more nucleotide sequences exogeneous to plasmid pF4.

6. The DNA of claim 1 consisting of nucleotides 2897–4015 of SEQ ID NO: 1 and optionally one or more nucleotide sequences exogeneous to plasmid pF4.

7. The DNA of claim 1 consisting of nucleotides 2897–3969 of SEQ ID NO: 1 and optionally one or more nucleotide sequences exogeneous to plasmid pF4.

8. A vector comprising the DNA of claim 1.

9. The vector of claim 8 that is a shuttle vector.

10. The vector of claim 9 that comprises a nucleotide sequence involved in autonomous replication in a bacterium other than Gluconobacter.

11. The vector of claim 8 that is a plasmid.

12. The vector of claim 8, further comprising a nucleotide sequence encoding one or more protein(s).

13. The vector of claim 12, wherein said one or more proteins are enzyme(s).

14. The vector of claim 13, wherein said enzyme(s) are L-sorbose dehydrogenase, L-sorbosone dehydrogenase, or both.

15. The vector of claim 14 that encodes L-sorbose dehydrogenase and L-sorbosone dehydrogenase.

16. A cell comprising the DNA of claim 1.

17. A cell comprising the vector of claim 8.

18. A method for producing one or more protein(s) comprising culturing a cell containing the vector of claim 12 for a time and under conditions suitable for expression of said protein(s), and harvesting or recovering the protein(s).

19. A method for producing L-sorbose dehydrogenase and/or L-sorbosone dehydrogenase, comprising culturing a cell containing the vector of claim 14 for a time and under conditions suitable for expression of L-sorbose dehydrogenase and/or L-sorbosone dehydrogenase, and harvesting or recovering L-sorbose dehydrogenase and/or L-sorbosone dehydrogenase.

20. A method for producing 2-keto-L-gulonic acid, comprising culturing a cell containing the vector of claim 15 for a time and under conditions suitable for the production of 2-keto-L-gulonic acid, and harvesting or recovering 2-keto-L-gulonic acid.

* * * * *

```
                              SEQUENCE LISTING

<160> NUMBER OF SEQ ID NOS: 42

<210> SEQ ID NO 1
<211> LENGTH: 4599
<212> TYPE: DNA
<213> ORGANISM: Gluconobacter oxydans

<400> SEQUENCE: 1
aagcttttca gatcaaaata ttaattattt atcgtctctt attgaaatat t tataaatgg      60 aaaaaatttc ccaattgatg gttttaaagt tgccttttcaa aatgatgatg g tgaaaccac   120 tatagaaaga aaaattatcc ccaaaatacc tttatacaaa aaaatttata a cagagttct   180 acatcctttt tcttcccgga cgccctaacg ggcgggctac gccgctcccg c gctgcgctc   240 gctccgggtc tgctctgctt tttgccgtaa agtctgcctg ctcatgacgc a aagaaattt   300 tagcggctaa aactaccgtt ttccggtagt atctgaactt gattaaacga a aggagctgc   360 atgatgagcg aagctctctc ccccatcgtc tccgagtttg agacggtcga a caggaagca   420 gcctataccg catggcttca ggccaaggtc gctgccagtc tggctgaccc g cgcccacca   480 atcccgcacg atgaggttga gcgacgtatg gccgaacggc tggccaagct t cgcaaacgc   540 aaggctgcct gatgctgcct atcgtctgga ccgaaaccgc tgacgaagat c ttgcaatca   600 tcacggaata cattggtgaa aacaatatcg gcgcagcgga gcggatgtgg t atcggctcc   660 gttcctgcgt tctgccctta tcggctcacc cctacctcta cccaatcagt g agcgggttc   720 ccggtttgcg cgaaatcgta gcccacccga attacatcat cctgtatcga g tgaccgcaa   780 ccagcgttga aatcattaat gtggttcatg cccgccgcca gttcccaagt t aaatactca   840 catccccggc ccgtaatccc atccactgtc gttccgttcc tcagcgactt c ttccgctgt   900 cactccccac ctatgaacgg cctgagcaat atcagcgatg aagggggcga c tacctcccg   960 gaagggttcc aaaatcgcag aaagcacacc acgactctgc tcggtgagcc g actggaata  1020 gtggattttc caccctgtct ccggcgcttc ctctgccccg atgacttccc g acgatagaa  1080 cgcatcggac ccggcttgca tcgctttgat tacgcctca ttggtggctt t cttggcttc  1140 tctggcttgc atttgcaggc ttgtggttgc ccgcaggatt tccgcacag t cggtgaaaa  1200 actgcctaca gcctccatca attcggcttt tcgctcttct ggcaaagacc g cttcatccg  1260 gggttgaatt ttgccatcca caagccgaag gcgaatgtca tctcttgcca c cgcttcgat  1320 ataatcagca gttttttgct cttttttttgt aatttcctgt tcgcgttggt t tagttcccg  1380 tgtcttggct gcaagcgcgg cttctcgcgc ttccatctct ccaaccaggt c tgcttttgc  1440 ggattccagt tttccccgtt cctgggtgat cttgtattct tccggctcca a ccgatccgg  1500 atcgcggccc accttcactt tgccccgctc gacccattct agccccatcc c gtcgcgcaa  1560 atggccggtc cataaatcct gaagggcacg cccctgaaaa acagggctgt c acatcgctc  1620 catgacgggc tgaccagcct tatcaaagac cagttcaaaa agaccggaat c cggattttt  1680 ctcttttttc tgccgctctc cgaaccgttc tagggccagt ttcttgccga a cttggacag  1740 gctgatccag tcctcaatca ccttcccgcg ccgggtagtc ttctcgtatt t cggtgcgaa  1800 gaagacatcg accccatgcc gtccggcttc atcccgatcc agtcgcgccc g aaaaacagc  1860
```

```
cctcccgcca tgtgttgcgt tgatgaaggc gacagcctca tccagcatcc g ttgttcgtt    1920 ctcaggggtg acaggcaggt ccgtggggaa ctgcaagaaa ccgtgccgtg c caaagcacg    1980 tccacccttg ttgcgcttcg tcccttcaac atgggcggca tagctctgtt c aagatccag    2040 cccctcgcca tacggactgt aaaccagtgg cggaacatcc cggatggccc t tttgctgcc    2100 agcgtaatcg aggcgctttt cgtgtcgccc catcgctgcc agacccgacg c atcgagcga    2160 tttcatccga acagacccag acttgcccct catattttct caccacaact c gtactgact    2220 tgatacaagt tggtatcctt tttataaaaa ggatacccgc tatccgtttt t tggaccta    2280 cccaaaaaca gcggacaagg ggagacccct ttgaaccccc ttcgaggact g aagatgaag    2340 gatggagaaa ttgcccgact gctgtccctg atcctgcggc acgagccaga a cggatcggc    2400 ctgacgctgg acggacaggg ctgggcgaac gtgcccgacc tgatccggct g gcgaaacga    2460 gcgggcaagc cgttcgacct cgacaccctg cgacgagtgg tcgagacgaa c gacaagcgg    2520 cgcttcaccc tctccccgga cggcctgcgc atcgggccg cacagggcca c tccctgtcg    2580 attgatctcg acctgcccgc cgtccagccg cccgagcggc tctggcatgg c accgcccgc    2640 gacaacctac cctcgatctt cagggatggt ctgaaaccgg tcgccgcca g atggtccac    2700 ctttccgacg accgggagac agcacagcgc gtcggtgagc gacacggaaa g gccgttatt    2760 ttggccgtag aagccggtct gatgtttcgg aataagattc ccttctatca g gctgacaac    2820 ggcgtctggc tcgttcctag cgtctctccg gcctatctgg cgttttgact g gaaacacgg    2880 actgttccca catactccct cccccttgagc aaatcctatc taacttgttc t gctgacctt    2940 gcagcaccag agcgagcgca gcgcgggagc ccgtaggcc gccgaaggcg t ctggtgtgg    3000 gataactctc ctcaaaaatg tctctgatcc gcccccgagg gtccacagga c ccgaggccc    3060 gctaccgctc acgagggcgt tcgcgggcct cgtcccgtgg gcttcgtgga c ggtccttaa    3120 gatcatagaa agagaaacaa aaaaggttgt tgtttatcag catgttatga g ggggggtg    3180 cctcaccagc tatgaggcag gggtgcctca tagctggtga ggcaggtttg a gctaaatct    3240 gctcattcaa tggcgatatt tatttcattt ttggaaaaat tcagctaata g atttgagcg    3300 aaatttgctc atgtcgtgag cagatatatt ttctttcggg tattttttct c tcacctatg    3360 aggcagggt gcctcatagg tggtgaggca tagggtgatg tggtgaagac t cgagaatta    3420 ggagtgacaa cagctccatc cggctcatgg gtgcaggtcg aacgagcagc a ttagaacgc    3480 tggtcacggt taggaatgga aaaaccctcg cgctgcatct gtgatgatga c actggtgca    3540 tcacatgggg cgcaataatg ctgtggtcgt gtcgcaaaaa acgcttgctg a actatgcgc    3600 gtgctcccgg gcaacgcttc aacgagcgct cgataccctt cggtcaggaa a ctggattga    3660 tgtccgccag atcggcccga ccggtactgc caacgcctac atcgtgaacc g cagggttgc    3720 atggtccgga gcaagagctg gacagcgtta cgctctattc gatgctgcgg t cgtggtctc    3780 agccacagaa cagccagacg ccgaaaccct agacgacctt cctccccttg a atccatccc    3840 ggcaatgttc aaaggcgaac gccagttacc gaccggcccc ggtatgccgc c cccttccca    3900 gccatctctt gacggtctgg aacctgactt gcccgccacc agccgcgacg a tcctgcaca    3960 gtgagcgcgc acaccctgc acacctatcg cctgcacagg ctgcacaggt a gctgacgtc    4020 tcccgctgga cgatcatgcg ggctataaaa tcatcagatt tgcaggcttt t cgggacaac    4080 aagaaccagt ggcggatcaa agctgacgat ctgaacgctt ggctagctgc a caccctgca    4140 cagtgtgcgc acactgtgca ggaagaaaac gatgcacacc ctgtgcacac c cccgcacac    4200
```

```
cccgatccga ttgcccaaga tacgcttgaa ctggtgcgcg tgaaggctga a ctcgaagcc    4260 gaaaagacgc tccgggcaac cgtcgaatct gaccgtgatc actggcgcga c cttgcgcag   4320 aaactggccg aatcacgacc acgcaaatgg tggttctggt aaattatatt a caacagtta   4380 actgtaattc ctagaaacag gaaaataaaa tagaaatgtc tgatagcatt t tagcaggaa   4440 taataggtgt agttgggaca gtaataggtt caactttaac atttactcta a acggaattt   4500 cttcttattt ctcacgaaaa agagaaaaga aagaaaaaga taaacaagag a aaagcgaa    4560 taagagaact atcaatagaa attgttgatg ctttatctg                          4599
```

<210> SEQ ID NO 2
<211> LENGTH: 19
<212> TYPE: DNA
<213> ORGANISM: Artificial Sequence
<220> FEATURE:
<221> NAME/KEY: misc_feature
<223> OTHER INFORMATION: Description of Artificial  Sequence: synthetic
      DNA

<400> SEQUENCE: 2
gataacaatt tcacacagg                                                19

<210> SEQ ID NO 3
<211> LENGTH: 17
<212> TYPE: DNA
<213> ORGANISM: Artificial Sequence
<220> FEATURE:
<221> NAME/KEY: misc_feature
<223> OTHER INFORMATION: Description of Artificial  Sequence: synthetic
      DNA

<400> SEQUENCE: 3
gttttcccag tcacgac                                                  17

<210> SEQ ID NO 4
<211> LENGTH: 15
<212> TYPE: DNA
<213> ORGANISM: Artificial Sequence
<220> FEATURE:
<221> NAME/KEY: misc_feature
<223> OTHER INFORMATION: Description of Artificial  Sequence: synthetic
      DNA

<400> SEQUENCE: 4
cgcgaccttg cgcag                                                    15

<210> SEQ ID NO 5
<211> LENGTH: 15
<212> TYPE: DNA
<213> ORGANISM: Artificial Sequence
<220> FEATURE:
<221> NAME/KEY: misc_feature
<223> OTHER INFORMATION: Description of Artificial  Sequence: synthetic
      DNA

<400> SEQUENCE: 5
gcctgctcat gacgc                                                    15

<210> SEQ ID NO 6
<211> LENGTH: 15
<212> TYPE: DNA
<213> ORGANISM: Artificial Sequence
<220> FEATURE:
<221> NAME/KEY: misc_feature
<223> OTHER INFORMATION: Description of Artificial  Sequence: synthetic
      DNA

<400> SEQUENCE: 6
cgatctgaac gcttg                                                    15

<210> SEQ ID NO 7
<211> LENGTH: 15
<212> TYPE: DNA
<213> ORGANISM: Artificial Sequence
<220> FEATURE:
<221> NAME/KEY: misc_feature
<223> OTHER INFORMATION: Description of Artificial  Sequence: synthetic
      DNA

<400> SEQUENCE: 7
caagcttcgc aaacg                                                    15

<210> SEQ ID NO 8
<211> LENGTH: 16
<212> TYPE: DNA
<213> ORGANISM: Artificial Sequence
<220> FEATURE:
<221> NAME/KEY: misc_feature
<223> OTHER INFORMATION: Description of Artificial  Sequence: synthetic
      DNA

<400> SEQUENCE: 8
ctgcacacct atcgcc                                                   16

<210> SEQ ID NO 9
<211> LENGTH: 15
<212> TYPE: DNA
<213> ORGANISM: Artificial Sequence
<220> FEATURE:
<221> NAME/KEY: misc_feature
<223> OTHER INFORMATION: Description of Artificial  Sequence: synthetic
      DNA

<400> SEQUENCE: 9
tgaccgcaac cagcg                                                    15

<210> SEQ ID NO 10
<211> LENGTH: 17
<212> TYPE: DNA
<213> ORGANISM: Artificial Sequence
<220> FEATURE:
<221> NAME/KEY: misc_feature
<223> OTHER INFORMATION: Description of Artificial  Sequence: synthetic
      DNA

<400> SEQUENCE: 10
aaggctgaac tcgaagc                                                  17

<210> SEQ ID NO 11
<211> LENGTH: 16
<212> TYPE: DNA
<213> ORGANISM: Artificial Sequence
<220> FEATURE:
<221> NAME/KEY: misc_feature
<223> OTHER INFORMATION: Description of Artificial  Sequence: synthetic
      DNA

<400> SEQUENCE: 11
atcccgcacg atgagg                                                   16

<210> SEQ ID NO 12
<211> LENGTH: 16
<212> TYPE: DNA

```
<213> ORGANISM: Artificial Sequence
<220> FEATURE:
<221> NAME/KEY: misc_feature
<223> OTHER INFORMATION: Description of Artificial  Sequence: synthetic
      DNA

<400> SEQUENCE: 12
acgagcgctc gatacc                                                          16

<210> SEQ ID NO 13
<211> LENGTH: 17
<212> TYPE: DNA
<213> ORGANISM: Artificial Sequence
<220> FEATURE:
<221> NAME/KEY: misc_feature
<223> OTHER INFORMATION: Description of Artificial  Sequence: synthetic
      DNA

<400> SEQUENCE: 13
acgaaaggag ctgcatg                                                         17

<210> SEQ ID NO 14
<211> LENGTH: 17
<212> TYPE: DNA
<213> ORGANISM: Artificial Sequence
<220> FEATURE:
<221> NAME/KEY: misc_feature
<223> OTHER INFORMATION: Description of Artificial  Sequence: synthetic
      DNA

<400> SEQUENCE: 14
gatgtggtga agactcg                                                         17

<210> SEQ ID NO 15
<211> LENGTH: 16
<212> TYPE: DNA
<213> ORGANISM: Artificial Sequence
<220> FEATURE:
<221> NAME/KEY: misc_feature
<223> OTHER INFORMATION: Description of Artificial  Sequence: synthetic
      DNA

<400> SEQUENCE: 15
tcagtgagcg ggttcc                                                          16

<210> SEQ ID NO 16
<211> LENGTH: 16
<212> TYPE: DNA
<213> ORGANISM: Artificial Sequence
<220> FEATURE:
<221> NAME/KEY: misc_feature
<223> OTHER INFORMATION: Description of Artificial  Sequence: synthetic
      DNA

<400> SEQUENCE: 16
gaaggcgtct ggtgtg                                                          16

<210> SEQ ID NO 17
<211> LENGTH: 17
<212> TYPE: DNA
<213> ORGANISM: Artificial Sequence
<220> FEATURE:
<221> NAME/KEY: misc_feature
<223> OTHER INFORMATION: Description of Artificial  Sequence: synthetic
      DNA

<400> SEQUENCE: 17
cggggttgaa ttttgcc                                                         17
```

<210> SEQ ID NO 18
<211> LENGTH: 16
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 18
cacaccacga ctctgc                                                   16

<210> SEQ ID NO 19
<211> LENGTH: 13
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 19
caggctgatc cag                                                      13

<210> SEQ ID NO 20
<211> LENGTH: 15
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 20
gcggctctgg catgg                                                    15

<210> SEQ ID NO 21
<211> LENGTH: 19
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 21
cgtactgact tgatacaag                                                19

<210> SEQ ID NO 22
<211> LENGTH: 15
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 22
ctgcgcaagg tcgcg                                                    15

<210> SEQ ID NO 23
<211> LENGTH: 15
<212> TYPE: DNA
<213> ORGANISM: Artificial Sequence
<220> FEATURE:
<221> NAME/KEY: misc_feature
<223> OTHER INFORMATION: Description of Artificial Sequence: synthetic

DNA

<400> SEQUENCE: 23
gcgtcatgag caggc                                                    15

<210> SEQ ID NO 24
<211> LENGTH: 15
<212> TYPE: DNA
<213> ORGANISM: Artificial Sequence
<220> FEATURE:
<221> NAME/KEY: misc_feature
<223> OTHER INFORMATION: Description of Artificial  Sequence: synthetic
      DNA

<400> SEQUENCE: 24
caagcgttca gatcg                                                    15

<210> SEQ ID NO 25
<211> LENGTH: 15
<212> TYPE: DNA
<213> ORGANISM: Artificial Sequence
<220> FEATURE:
<221> NAME/KEY: misc_feature
<223> OTHER INFORMATION: Description of Artificial  Sequence: synthetic
      DNA

<400> SEQUENCE: 25
cgtttgcgaa gcttg                                                    15

<210> SEQ ID NO 26
<211> LENGTH: 16
<212> TYPE: DNA
<213> ORGANISM: Artificial Sequence
<220> FEATURE:
<221> NAME/KEY: misc_feature
<223> OTHER INFORMATION: Description of Artificial  Sequence: synthetic
      DNA

<400> SEQUENCE: 26
gagatggctg ggaagg                                                   16

<210> SEQ ID NO 27
<211> LENGTH: 16
<212> TYPE: DNA
<213> ORGANISM: Artificial Sequence
<220> FEATURE:
<221> NAME/KEY: misc_feature
<223> OTHER INFORMATION: Description of Artificial  Sequence: synthetic
      DNA

<400> SEQUENCE: 27
tggcctgaag ccatgc                                                   16

<210> SEQ ID NO 28
<211> LENGTH: 15
<212> TYPE: DNA
<213> ORGANISM: Artificial Sequence
<220> FEATURE:
<221> NAME/KEY: misc_feature
<223> OTHER INFORMATION: Description of Artificial  Sequence: synthetic
      DNA

<400> SEQUENCE: 28
gatgcagcgc gaggg                                                    15

<210> SEQ ID NO 29
<211> LENGTH: 17

```
<212> TYPE: DNA
<213> ORGANISM: Artificial Sequence
<220> FEATURE:
<221> NAME/KEY: misc_feature
<223> OTHER INFORMATION: Description of Artificial  Sequence: synthetic
      DNA

<400> SEQUENCE: 29
tcatgcagct cctttcg                                                    17

<210> SEQ ID NO 30
<211> LENGTH: 16
<212> TYPE: DNA
<213> ORGANISM: Artificial Sequence
<220> FEATURE:
<221> NAME/KEY: misc_feature
<223> OTHER INFORMATION: Description of Artificial  Sequence: synthetic
      DNA

<400> SEQUENCE: 30
tcaccagcta tgaggc                                                     16

<210> SEQ ID NO 31
<211> LENGTH: 16
<212> TYPE: DNA
<213> ORGANISM: Artificial Sequence
<220> FEATURE:
<221> NAME/KEY: misc_feature
<223> OTHER INFORMATION: Description of Artificial  Sequence: synthetic
      DNA

<400> SEQUENCE: 31
gccgatacca catccg                                                     16

<210> SEQ ID NO 32
<211> LENGTH: 17
<212> TYPE: DNA
<213> ORGANISM: Artificial Sequence
<220> FEATURE:
<221> NAME/KEY: misc_feature
<223> OTHER INFORMATION: Description of Artificial  Sequence: synthetic
      DNA

<400> SEQUENCE: 32
cgagtcttca ccacatc                                                    17

<210> SEQ ID NO 33
<211> LENGTH: 16
<212> TYPE: DNA
<213> ORGANISM: Artificial Sequence
<220> FEATURE:
<221> NAME/KEY: misc_feature
<223> OTHER INFORMATION: Description of Artificial  Sequence: synthetic
      DNA

<400> SEQUENCE: 33
gatggaggct gtaggc                                                     16

<210> SEQ ID NO 34
<211> LENGTH: 16
<212> TYPE: DNA
<213> ORGANISM: Artificial Sequence
<220> FEATURE:
<221> NAME/KEY: misc_feature
<223> OTHER INFORMATION: Description of Artificial  Sequence: synthetic
      DNA

<400> SEQUENCE: 34
```

```
ctctggtgct gcaagg                                              16
```

<210> SEQ ID NO 35
<211> LENGTH: 16
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 35

```
gaacggttcg gagagc                                              16
```

<210> SEQ ID NO 36
<211> LENGTH: 17
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 36

```
ccacaccaga cgccttc                                             17
```

<210> SEQ ID NO 37
<211> LENGTH: 17
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 37

```
tcgattacgc tggcagc                                             17
```

<210> SEQ ID NO 38
<211> LENGTH: 16
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 38

```
aggtggacca tctggc                                              16
```

<210> SEQ ID NO 39
<211> LENGTH: 17
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 39

```
atccgcaaaa gcagacc                                             17
```

<210> SEQ ID NO 40
<211> LENGTH: 18
<212> TYPE: DNA
<213> ORGANISM: Artificial Sequence
<220> FEATURE:
<221> NAME/KEY: misc_feature -continued

```
<223> OTHER INFORMATION: Description of Artificial  Sequence: synthetic
      DNA

<400> SEQUENCE: 40
gtttccagtc aaaacgcc                                                       18

<210> SEQ ID NO 41
<211> LENGTH: 15
<212> TYPE: DNA
<213> ORGANISM: Artificial Sequence
<220> FEATURE:
<221> NAME/KEY: misc_feature
<223> OTHER INFORMATION: Description of Artificial  Sequence: synthetic
      DNA

<400> SEQUENCE: 41
cgggtcctgt ggacc                                                          15

<210> SEQ ID NO 42
<211> LENGTH: 14
<212> TYPE: DNA
<213> ORGANISM: Artificial Sequence
<220> FEATURE:
<221> NAME/KEY: misc_feature
<223> OTHER INFORMATION: Description of Artificial  Sequence: synthetic
      DNA

<400> SEQUENCE: 42
cggaattccg tgca                                                           14
```